United States Patent
Fritsch

(12) 
(10) Patent No.: US 6,195,828 B1
(45) Date of Patent: Mar. 6, 2001

(54) BRUSH SECTION FOR AN ELECTRONIC TOOTHBRUSH

(75) Inventor: Thomas Fritsch, Eppstein (DE)

(73) Assignee: Braun GmbH (DE)

( * ) Notice: Subject to any disclaimer, the term of this patent is extended or adjusted under 35 U.S.C. 154(b) by 0 days.

(21) Appl. No.: 09/425,262

(22) Filed: Oct. 22, 1999

Related U.S. Application Data

(63) Continuation-in-part of application No. PCT/EP98/01374, filed on Mar. 10, 1998.

(30) Foreign Application Priority Data

Apr. 24, 1997 (DE) .............................................. 197 17 334

(51) Int. Cl.[7] .............................. A46B 13/02; A61C 17/34
(52) U.S. Cl. ............................................... 15/22.1; 15/28
(58) Field of Search ..................... 15/22.1, 22.2, 15/28, 29, 22.4

(56) References Cited

U.S. PATENT DOCUMENTS

| | | | |
|---|---|---|---|
| 2,766,470 | 10/1956 | Baker | 15/28 |
| 5,504,961 | 4/1996 | Yang | 15/28 |
| 5,577,285 | 11/1996 | Drossler | 15/22 |
| 5,732,432 | * 3/1998 | Hui | 15/28 |
| 5,842,244 | * 12/1998 | Hilfinger et al. | 15/28 |
| 5,974,613 | * 11/1999 | Herzog | 15/28 |

FOREIGN PATENT DOCUMENTS

| | | |
|---|---|---|
| 497 153 | 11/1970 | (CH) . |
| 44 09 817 C1 | 7/1995 | (DE) . |
| WO 94/12121 | 6/1994 | (WO) . |
| WO 96/37164 | 11/1996 | (WO) . |

\* cited by examiner

Primary Examiner—Gary K. Graham
(74) Attorney, Agent, or Firm—Edward S. Podszus

(57) ABSTRACT

The invention is directed to a brush section (1) for an electric toothbrush. The brush section (1) has a mounting tube (2) in which is accommodated an actuatable plug-on shaft (3) mounted for rotation about a longitudinal axis (4), said shaft being equipped with a driving element (24) arranged eccentrically to the longitudinal axis (4). Further, the brush section (1) has a bristle carrier (8) mounted for rotation about a transverse axis (10) and equipped with a driven element (22) arranged eccentrically to the transverse axis (10) and coupled with the driving element (24). In this arrangement, a rotary movement (5) of the plug-on shaft (3) about the longitudinal axis (4) produces a rotary movement (25) of the bristle carrier (8) about the transverse axis (10. The plug-on shaft (3) and the bristle carrier (8) are braced against each other and/or against the mounting tube (2) by spring means. This prevents the occurrence of rattling noises in activated condition of the electric toothbrush.

27 Claims, 5 Drawing Sheets

BRUSH SECTION FOR AN ELECTRONIC TOOTHBRUSH

This application is a continuation of International Application PCT/EP98/01374, pending, with an International filing date of Mar. 10, 1998.

BACKGROUND OF THE INVENTION

This invention relates to a brush section for an electric toothbrush, having a mounting tube in which is accommodated an actuatable plug-on shaft mounted for rotation about a longitudinal axis, said shaft being equipped with a driving element arranged eccentrically to the longitudinal axis, having a bristle carrier mounted for rotation about a transverse axis and equipped with a driven element arranged eccentrically to the transverse axis and coupled with the driving element, whereby a rotary movement of the plug-on shaft about the longitudinal axis produces a rotary movement of the bristle carrier about the transverse axis.

A brush section of this type is known from the international patent application WO 94/12121. With the brush section attached to an electric toothbrush and the electric toothbrush in operation, the plug-on shaft performs an oscillating rotary movement. This rotary movement is transmitted by the driving element to the driven element and by the driven element to the bristle carrier. Hence the bristle carrier also performs an oscillating rotary movement with its tufts of bristles projecting in the direction of the transverse axis.

On the brush section known from the international patent application WO 94/12121 the mounting tube forms a fixed component whereas the plug-on shaft, the bristle carrier, the driving element and the driven element are moving components. These moving components have a clearance in their bearings and are able to perform free movements within the limits of this clearance. In doing so, they knock against each other or against the fixed component(s). This results in rattling noises when the electric toothbrush is in operation.

SUMMARY OF THE INVENTION

It is an object of the present invention to provide a brush section for an electric toothbrush in which there are no or as close to no rattling noises when the electric toothbrush is in operation.

According to the present invention this object is accomplished with a brush section for an electric toothbrush of the type initially referred to by having the plug-on shaft and the bristle carrier braced (or biased) against each other and/or against the mounting tube.

As the result of the bracing the plug-on shaft and the bristle carrier are urged against their bearings. Consequently, when the electric toothbrush is not in operation the two components are no longer able to perform any free movements in their bearings in spite of the existing clearance. Even when the electric toothbrush is in operation the two components continue to be urged against their bearings. Consequently, friction is generated in the bearings, preventing or at least reducing the occurrence of free movements by the plug-on shaft and the bristle carrier in their bearings. Bumping or knocking of the moving components against each other or against the fixed component(s) is thus prevented, which means that there are no longer any rattling noises.

It is possible for only the plug-on shaft or only the bristle carrier to be separately braced against the mounting tube. This results in only the one or other of the two components no longer making any rattling noises. It is also possible for the plug-on shaft and the bristle carrier to be braced against each other, that is, independently of the mounting tube, and for rattling to be prevented in this way. Yet another possibility is to jointly brace the plug-on shaft and the bristle carrier against the mounting tube and to prevent rattling in this way.

In an advantageous aspect of the present invention the plug-on shaft, the bristle carrier, the driving element and the driven element are braced against each other and/or against the mounting tube. Consequently, there is no longer any rattling caused by these components.

It is possible for the plug-on shaft, the bristle carrier, the driving element and the driven element each to be separately braced against the mounting tube. It is also possible for these components to be braced against each other, that is, independently of the mounting tube. Yet another possibility is to jointly brace the components mentioned against the mounting tube.

It is particularly suitable to provide spring means for the bracing. This represents a particularly simple way and means of bracing the respective components against each other. Furthermore, the spring means may be accommodated in the interior of the mounting tube, enabling them to be structurally integrated in the known brush section without any major effort.

In an advantageous further aspect of the present invention provision is made for a helical compression spring held on the side of the driving element remote from the driven element and bearing against the plug-on shaft. It is particularly convenient in this connection for the helical compression spring to be held by an enlargement of the driving element or by a sleeve fitted onto the driving element. With this further configuration the bracing of the components can be effected particularly simply and economically.

In further advantageous aspects of the present invention provision is made for a helical compression spring arranged on the side of the driving element close to the driven element and bearing against the driven element and the plug-on shaft. It is also possible to provide a helical tension spring held on the side of the driving element remote from the driven element and on the plug-on shaft. These further configurations are likewise simple and low-cost possibilities for bracing the components.

Particularly conveniently, the driving element and the driven element are fixedly joined together. In this manner the driving element and the driven element are unable to knock against each other and cause any rattling noises.

Further features, application possibilities and advantages of the present invention will become apparent from the subsequent description of embodiments of the invention illustrated in the Figures of the accompanying drawing. It will be understood that any single feature and any combination of single features described or represented by illustration form the subject-matter of the present invention, irrespective of their summary in the patent claims or their back-reference, and irrespective of their wording and representation in the description and the drawing, respectively.

DETAILED DESCRIPTION OF PREFERRED EMBODIMENTS

The subsequent description of embodiments of brush sections in accordance with the invention is based on the international patent application WO 94/12121 initially referred to as prior art, whose disclosure content is hereby incorporated in its entirety in the disclosure content of the present description by express reference. Attention is drawn in particular to the general description of the electric toothbrush and the brush section in the international patent application WO 94/12121 and to the embodiments of FIGS. 7a to 7e, FIGS. 8a to 8e and FIG. 9 of the international patent application WO 94/12121.

Figure 1:
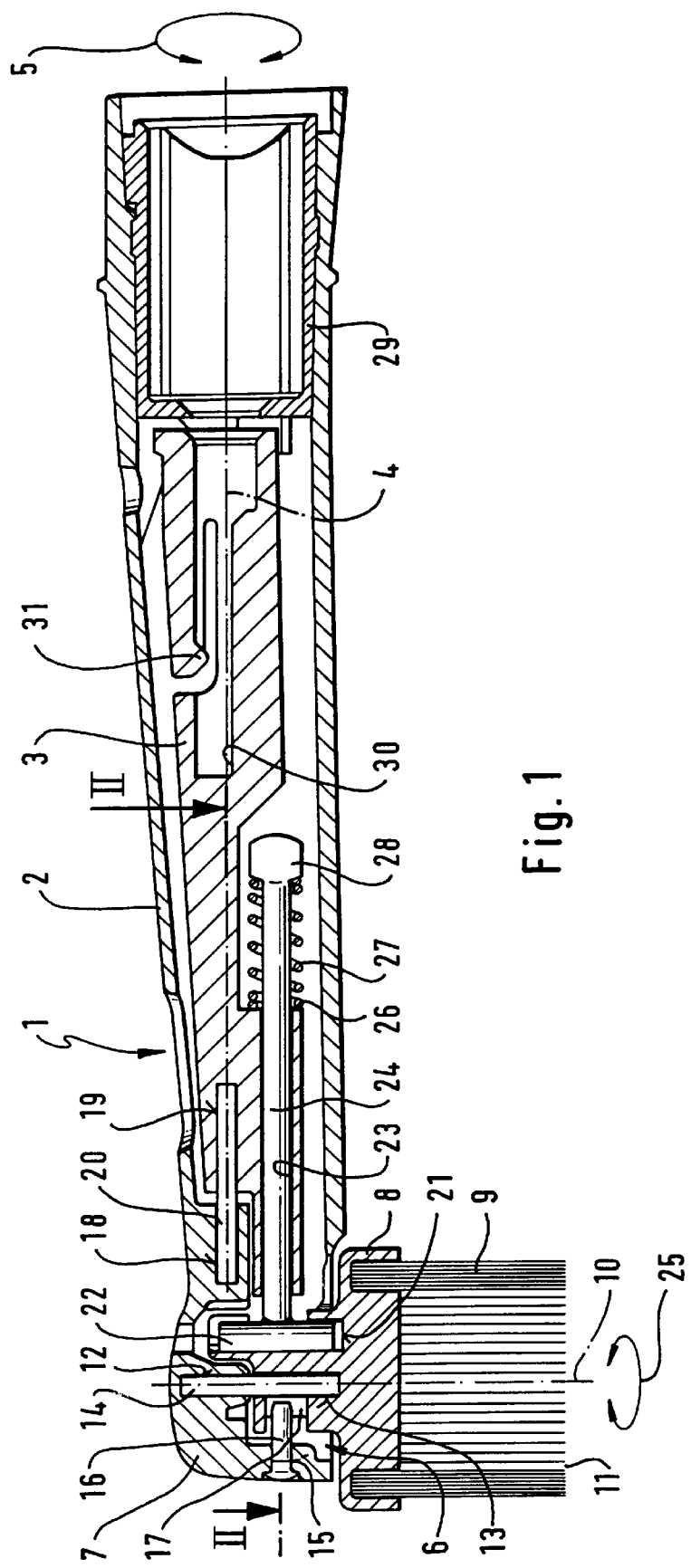
FIG. 1 is a schematic longitudinal sectional view of a first embodiment of a brush section of the present invention for an electric toothbrush, taken along the plane I—I of FIG. 2.
Figure 2:
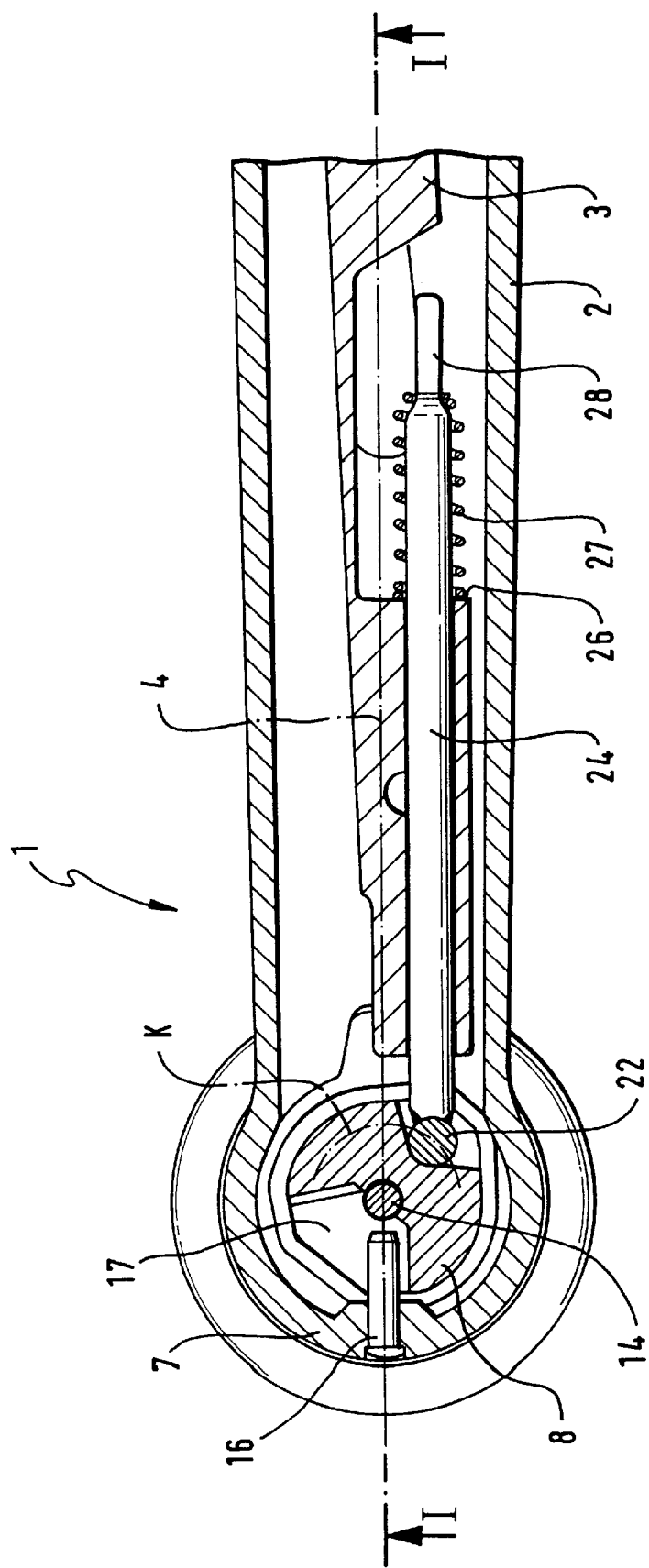
FIG. 2 is a schematic longitudinal sectional view of the brush section of FIG. 1, taken along the plane II—II of FIG. 1.

FIGS. 1 and 2 show a first embodiment of a brush section 1 adapted to be plugged on a handle section of an electric toothbrush.

The brush section 1 has a mounting tube 2 accommodating a plug-on shaft 3. The mounting tube 2 and the plug-on shaft 3 extend approximately in the direction of a longitudinal axis 4. The plug-on shaft 3 is adapted to be coupled with an electric motor accommodated in the handle section, which under operating conditions sets the plug-on shaft in an oscillating rotary movement about the longitudinal axis 4. This is indicated in FIG. 1 by an arrow 5.

At its end remote from the handle section of the electric toothbrush the mounting tube 2 is transformed into a cup-shaped holder 7 having an opening 6 in which a bristle carrier 8 is accommodated. The bristle carrier 8 is constructed in the form of a disk covering the opening 6 of the holder 7. Projecting in the direction of a transverse axis 10 from the side of the bristle carrier 8 facing away from the holder 7 are a plurality of bristle tufts 9 whose free ends form a bristle surface 11. The transverse axis 10 is arranged at an angle of around 90 degrees to the longitudinal axis 4.

Blind holes 12, 13 in relative alignment and disposed coaxially to the transverse axis 10 are provided in the holder 7 and in the bristle carrier 8, respectively. Securely press-fitted in the blind hole 12 of the holder 7 is a pin 14 which has sufficient clearance in the blind hole 13 of the bristle carrier 8 to enable the bristle carrier 8 to swivel about the pin 14 and hence about the transverse axis 10.

The holder 7 is provided with a bore 15 extending approximately parallel to the longitudinal axis 4 and having a lock pin 16 securely press-fitted therein. The lock pin 16 engages in a groove 17 provided in the bristle carrier 8, thus holding the bristle carrier 8 on the pin 14 and hence in the holder 7.

The end of the mounting tube 2 close to the holder 7 and the plug-on shaft 3 are provided with blind holes 18, 19 in relative alignment and disposed coaxially to the longitudinal axis 4. Securely press-fitted in the blind hole 19 of the plug-on shaft 3 is a pin 20 which has sufficient clearance in the blind hole 18 of the mounting tube 2 to enable the plug-on shaft 3 to swivel with the pin 20 about the longitudinal axis 4.

At a distance from the transverse axis 10 the bristle carrier 8 is provided with a blind hole 21 arranged approximately parallel to the transverse axis 10 and accommodating a trunnion-shaped driven element 22 with clearance to swivel and to slide longitudinally. At a distance from the longitudinal axis 4 the plug-on shaft 3 is provided with a passage bore 23 arranged approximately parallel to the longitudinal axis 4 and accommodating a pin-shaped driving element 24 with clearance to swivel and to slide longitudinally. The driven element 22 and the driving element 24 are fixedly joined together at an angle of 90 degrees, approximately.

When the plug-on shaft 3 is set in the oscillating rotary movement 5 about the longitudinal axis 4 as mentioned above, this movement is transmitted via the driving element 24 and the driven element 22 to the bristle carrier 8. The bristle carrier then executes an oscillating rotary movement about the transverse axis 10. This is indicated in FIG. 1 by the arrow 25. The rotary movement 5 of the plug-on shaft 3 and the rotary movement 25 of the bristle carrier 8 have the same frequency and the same phase but their amplitudes may differ.

The free end of the pin-shaped driving element 24 remote from the driven element 22 projects out of the passage bore 23 of the plug-on shaft 3, extending a little beyond an edge 26 of the plug-on shaft 3. A helical compression spring 27 is mounted on the driving element 24 in the area of the projecting piece. The free end of the driving element 24 is compressed and flattened, forming an enlargement 28. The helical compression spring 27 thus rests with one of its ends against the enlargement 28 and is held by it. At the same time the helical compression spring 27 bears with its other end against the edge 26 of the plug-on shaft 3.

The force of the helical compression spring 27 acts in the direction of the longitudinal axis 4, urging the enlargement 28 of the driving element 24 away from the edge 26 of the plug-on shaft 3. The force of the helical compression spring 27 thus acts in a direction approximately transverse to the driven element 22 connected with the driving element 24 and to the pin 14 supporting the bristle carrier 8. Furthermore the force of the helical compression spring 27 acts approximately parallel to the pin 20 supporting the plug-on shaft 3. Under operating conditions the force of the helical compression spring 27 produces a friction between the driven element 22 and the blind hole 21 in the bristle carrier 8, and a friction between the pin 14 and the blind hole 13 in the bristle carrier 8. In addition, friction occurs also between the front end of the pin 20 and the blind hole 18 of the mounting tube 2.

The plug-on shaft 3 and the bristle carrier 8 are braced (biased) together by the force of the helical compression spring 27 and particularly by the friction occurring under operating conditions. Moreover, the driven element 22 and the driving element 24 are also braced with the plug-on shaft 3 and the bristle carrier 8 by the force of the helical compression spring 27. In this arrangement, the bracing (biasing) acts between the moving components identified as well as between these moving components and the fixed mounting tube 2 of the brush section 1. Free movements of the components referred to are prevented by the force of the helical compression spring 27 and the resultant bracing.

As the result, the plug-on shaft 3 and the bristle carrier 8 are no longer able to move freely in their bearings in spite of the clearance. In particular, the pin 14 is no longer able, in spite of its clearance, to move freely in the blind hole 13 of the bristle carrier 8 as the result of the friction. Similarly, the pin 20 is no longer able, in spite of its clearance, to move freely in the blind hole 18 of the mounting tube 2 as the result of the friction. Bracing of the plug-on shaft 3 and the bristle carrier 8 thus prevents free movements, making it impossible for the plug-on shaft 3 or the bristle carrier 8 to knock against any other components and cause attendant rattling noises.

The driven element 22 and the driving element 24 are likewise unable, in spite of the clearance, to move freely in their bearings. In particular the driven element 22 is no longer able, in spite of the clearance, to move freely in the blind hole 21 as the result of the friction. Similarly, the driving element 24 is no longer able, in spite of the clearance, to move freely in the passage bore 23 on account of the force of the helical compression spring 27. Bracing of the driven element 22 and the driving element 24 as well as their fixed connection thus prevent free movements, making it impossible for them to knock against any other components and cause attendant rattling noises.

Even after the brush section 1 has been used for a long time and the bearings of the plug-on shaft 3, the bristle carrier 8, the driven element 22 and the driving element 24 have been worn in particular by the abrasives contained in the toothpaste, the larger clearance of said components resulting therefrom is compensated for by the bracing effected by the helical compression spring 27. Hence the bracing of said components will still prevent rattling noises even after the brush section 1 has been used for a long time.

As becomes apparent particularly from FIG. 2, the driven element 22 executes an oscillating rotary movement on an orbit K about the transverse axis 10 under operating conditions. During this rotary movement the helical compression spring 27 is thereby compressed and relieved in alternation. The helical compression spring 27 is compressed most at the two reversing points of the rotary movement, meaning that it exerts its greatest force at these points. Excessive vibration of the bristle carrier 8 under operating conditions is thus prevented.

As previously described, the brush section 1 is attachable to the electric toothbrush. For this purpose the mounting tube 2 is equipped at its end close to the toothbrush with a profile ring 29 into which a neck formed at the forward end of the toothbrush can be inserted. The profile ring 29 transmits forces and moments between the mounting tube 2 of the brush section 1 and the neck of the electric toothbrush. At its end close to the toothbrush the plug-on shaft 3 has a blind hole concentric with the longitudinal axis 4 and having a flattened zone 30 for engagement with the drive shaft moved by an electric motor accommodated in the toothbrush. The flattened zone 30 transmits torque and rotary movement from the drive shaft of the toothbrush to the plug-on shaft 3 of the mouthpiece 1.

Furthermore, the plug-on shaft 3 is equipped with a hook 31 projecting into the flattened zone 30 for engagement with a registering notch of the toothbrush drive shaft, thereby fixedly securing the plug-on shaft 3 and hence the brush section 1 on the drive shaft of the electric toothbrush. The clearance of the plug-on shaft 3 within the mounting tube 2 in the direction of the longitudinal axis 4 is absorbed by the bracing effected by means of the helical compression spring 27. Consequently, the plug-on shaft 3 and hence the brush section 1 are arranged without clearance on the drive shaft of the electric toothbrush. There is no wobbling, therefore, between the brush section 1 and the handle section of the electric toothbrush.

Figure 3:
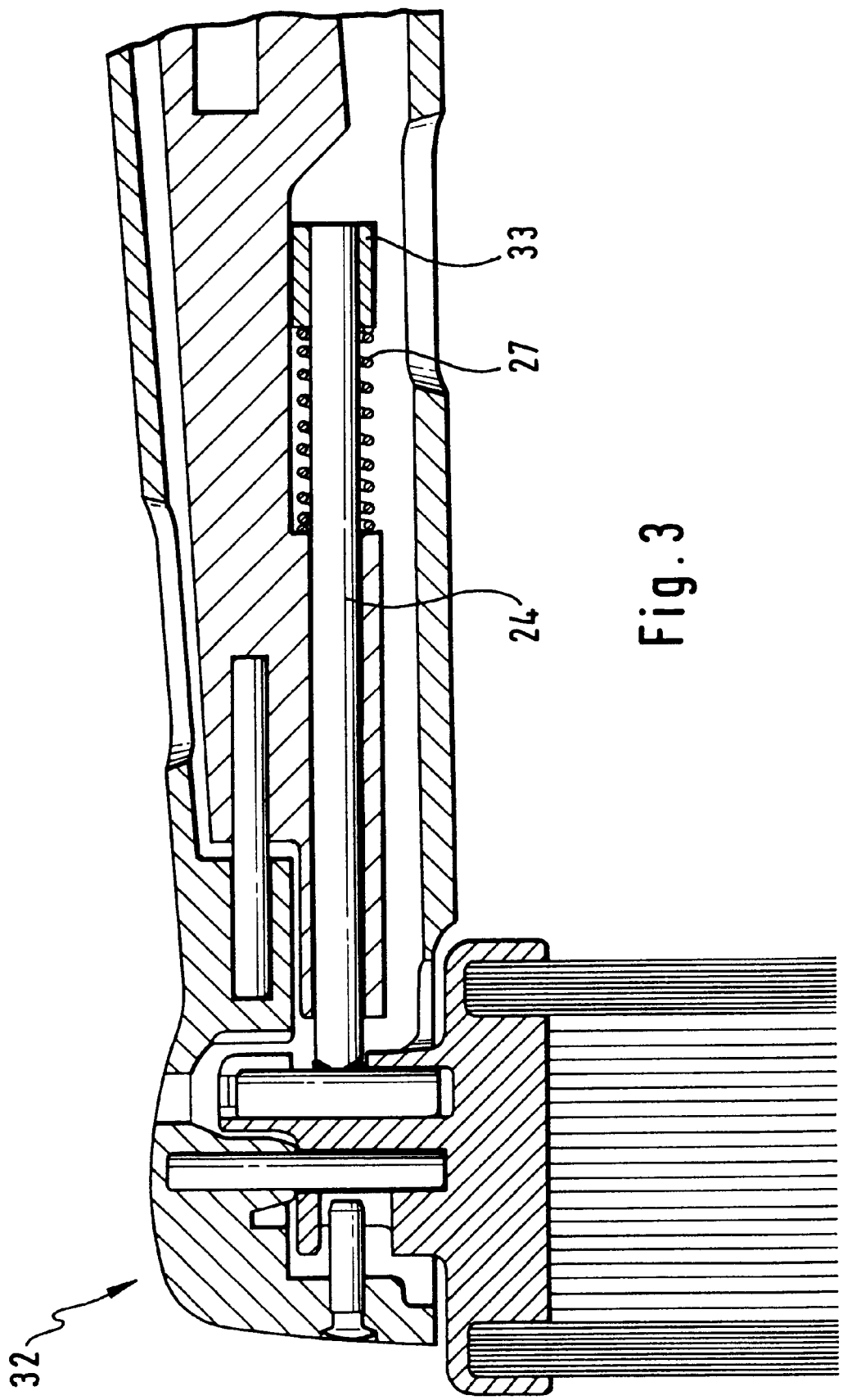
FIG. 3 is a schematic longitudinal sectional view of a second embodiment of a brush section of the present invention for an electric toothbrush.

FIG. 3 shows a second embodiment of a brush section 32 attachable to a handle section of an electric toothbrush. The brush section 32 of FIG. 3 differs from the brush section 1 of FIGS. 1 and 2 only to the extent that with the brush section 32 a sleeve 33 is securely press-fitted onto the free end of the driving element 24 to secure the helical compression spring 27, instead of using the enlargement 28 of the brush section 1.

Figure 4:
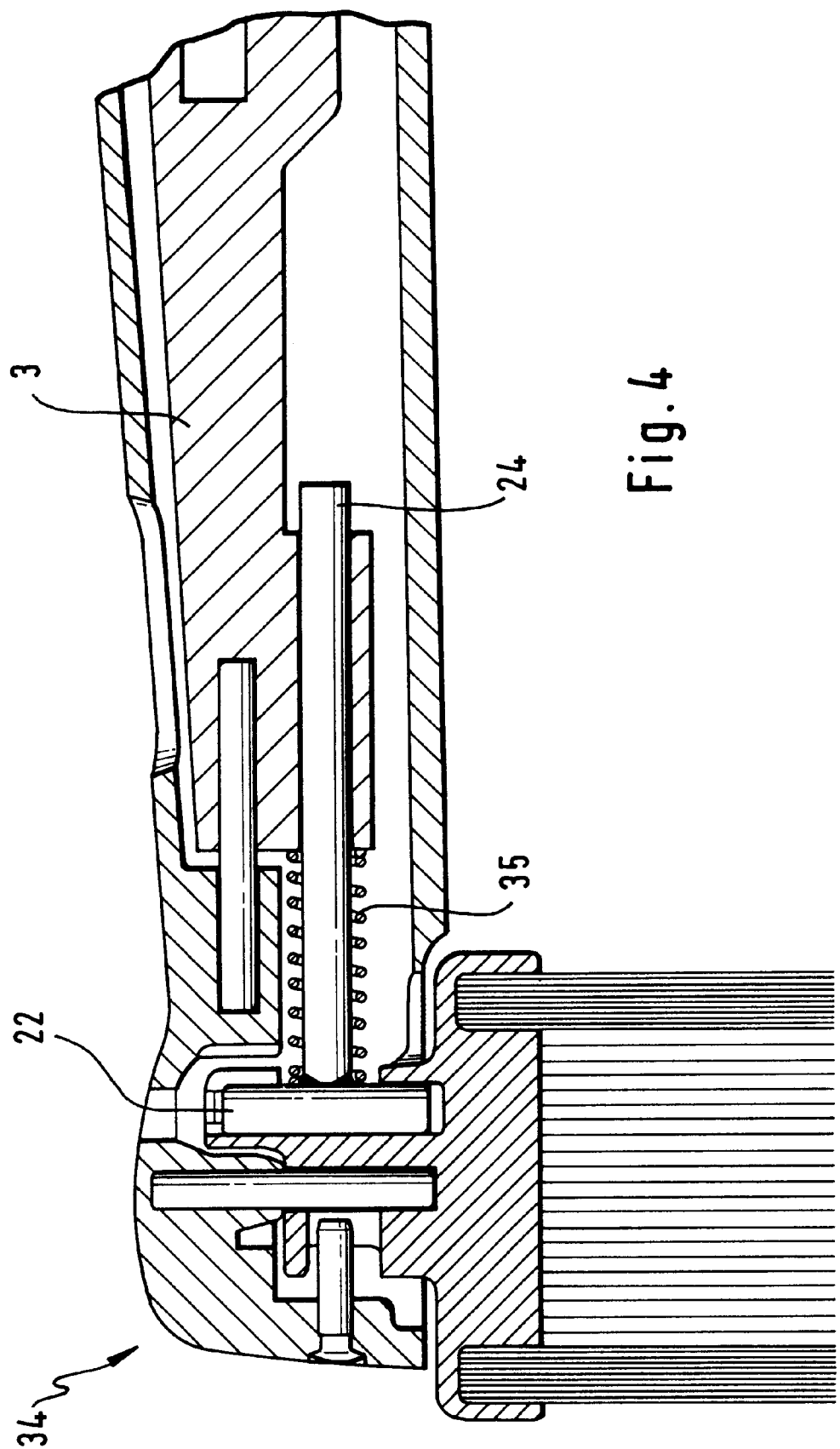
FIG. 4 is a schematic longitudinal sectional view of a third embodiment of a brush section of the present invention for an electric toothbrush.

FIG. 4 shows a third embodiment of a brush section 34 attachable to a handle section of an electric toothbrush. The brush section 34 of FIG. 4 differs from the brush section 1 of FIGS. 1 and 2 only to the extent that with the brush section 34 a helical compression spring 35 is arranged on the side of the driving element 24 close to the driven element 22, that is, between the driven element 22 and the plug-on shaft 3, instead of using the helical compression spring 27 fitted to the portion of the driving element 24 projecting beyond the edge 26 of the plug-on shaft 3. The helical compression spring 35 thus bears against the driven element 22 and the plug-on shaft 3.

Figure 5:
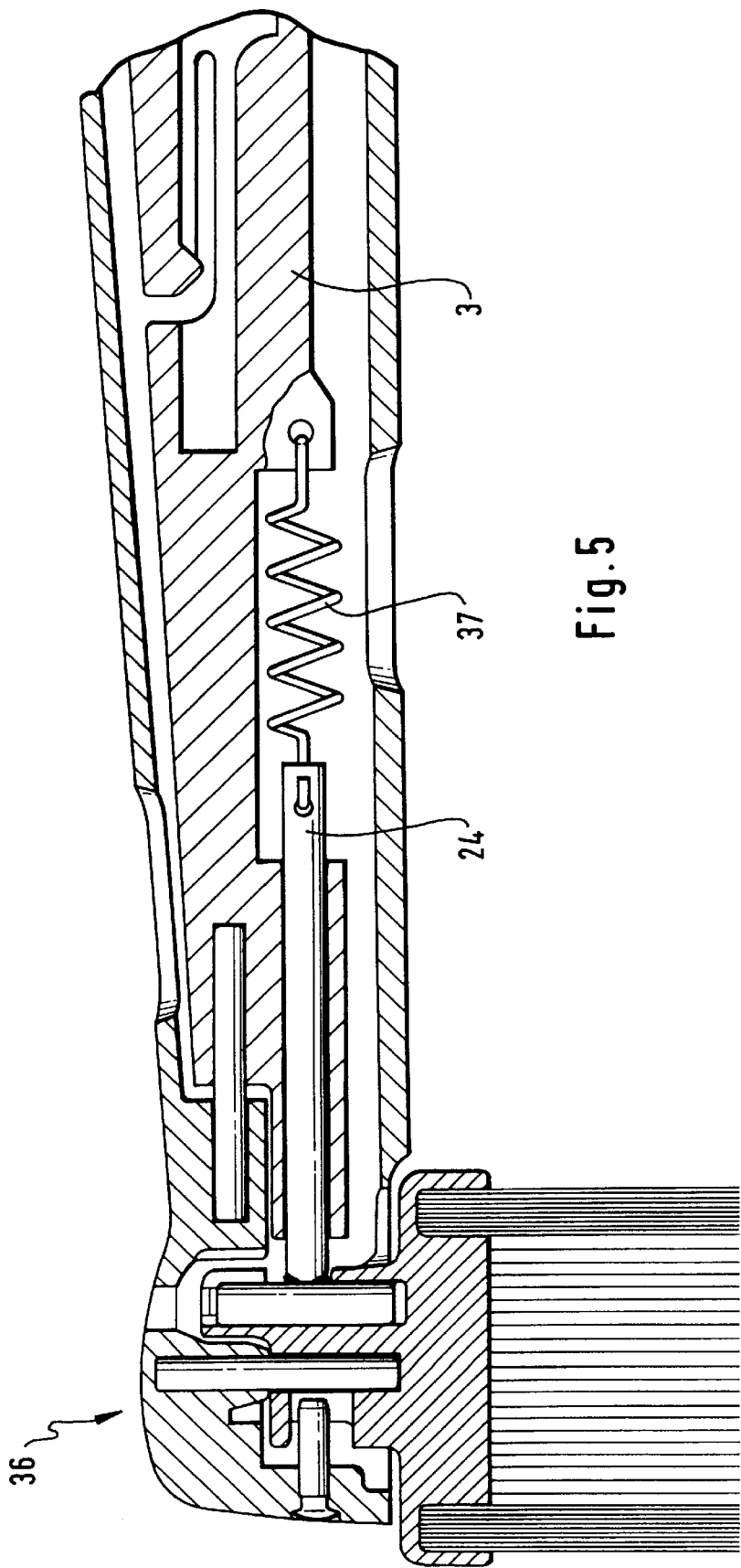
FIG. 5 is a schematic longitudinal sectional view of a fourth embodiment of a brush section of the present invention for an electric toothbrush.

FIG. 5 shows a fourth embodiment of a brush section 36 attachable to a handle section of an electric toothbrush. The brush section 36 of FIG. 5 differs from the brush section 1 of FIGS. 1 and 2 only to the extent that with the brush section 36 provision is made for a helical tension spring 37 held on the side of the driving element 24 remote from the driven element 22 and on the plug-on shaft 3, instead of using the helical compression spring 27 of the brush section 1. For mounting, the helical tension spring 37 is passed through openings in the driving element 24 and in the plug-on shaft 3.

What is claimed is:

1. A brush section for an electric toothbrush, comprising a mounting tube (2) in which is disposed an actuatable plug-on shaft (3) mounted for rotation about a longitudinal axis (4), said shaft comprising a driving element (24) arranged about the longitudinal axis (4), a bristle carrier (8) mounted for rotation about a transverse axis (10) and comprising a driven element (22) arranged about the transverse axis (10) and coupled with the driving element (24), whereby a rotary movement of the plug-on shaft (3) about the longitudinal axis (4) produces a rotary movement of the bristle carrier (8) about the transverse axis (10), and wherein the plug-on shaft (3) and the bristle carrier (8) are braced against each other.

2. The brush section according to claim 1, wherein the plug-on shaft (3), the bristle carrier (8), the driving element (24) and the driven element (22) are braced against each other.

3. The brush section according to claim 2, wherein the plug-on shaft (3), the bristle carrier (8), the driving element (24) and the driven element (22) further are braced against the mounting tube (2).

4. The brush section according to claim 1, wherein the plug-on shaft (3) and the bristle carrier (8) further are braced against the mounting tube (2).

5. The brush section according to claim 1, wherein the plug-on shaft (3), the bristle carrier (8), the driving element (24) and the driven element (22) are braced against the mounting tube (2).

6. The brush section according to claim 1, claim 2, claim 4, claim 5 or claim 3, wherein a biasing spring provides the bracing.

7. The brush section according to claim 1, wherein a helical compression spring (27) is held on the side of the driving element (24) remote from the driven element (22) and bearing against the plug-on shaft (3).

8. The brush section according to claim 7, wherein the helical compression spring (27) is held by an enlargement (28) of the driving element (24) or by a sleeve (33) press-fitted onto the driving element (24).

9. The brush section according to claim 1, wherein a helical compression spring (35) is arranged on the side of the driving element (24) close to the driven element (22) and bearing against the driven element (22) and the plug-on shaft (3).

10. The brush section according to claim 1, wherein a helical tension spring (37) is held on the side of the driving element (24) remote from the driven element (22) and on the plug-on shaft (3).

11. The brush section according to claim 1, wherein the driving element (24) and the driven element (22) are fixedly joined together.

12. The brush section according to claim 1 in combination with an electric toothbrush, the brush section adapted to be coupled therewith.

13. The brush section according to claim 1, wherein the transverse axis extends at an angle of about 90° to the longitudinal axis.

14. The brush section according to claim 1, wherein the driven element is arranged eccentrically to the transverse axis and the driving element is arranged eccentrically to the longitudinal axis.

15. A brush section for an electric toothbrush, comprising
- a mounting tube (2) in which is disposed an actuatable plug-on shaft (3) mounted for rotation about a longitudinal axis (4), said shaft comprising a driving element (24) arranged about the longitudinal axis (4),
- a bristle carrier (8) mounted for rotation about a transverse axis (10) and comprising a driven element (22) arranged about the transverse axis (10) and coupled with the driving element (24),
- whereby a rotary movement of the plug-on shaft (3) about the longitudinal axis (4) produces a rotary movement of the bristle carrier (8) about the transverse axis (10), and
- wherein the plug-on shaft (3) and the bristle carrier (8) are braced against the mounting tube (2).

16. The brush section according to claim 15, wherein the plug-on shaft (3), the bristle carrier (8), the driving element (24) and the driven element (22) are braced against each other.

17. The brush section according to claim 15, wherein the plug-on shaft (3), the bristle carrier (8), the driving element (24) and the driven element (22) are braced against the mounting tube (2).

18. The brush section according to claim 16, wherein the plug-on shaft (3), the bristle carrier (8), the driving element (24) and the driven element (22) further are braced against the mounting tube (2).

19. The brush section according to any of claims 15 through 18, wherein a biasing spring provides the bracing.

20. The brush section according to claim 15 wherein a helical compression spring (27) is held on the side of the driving element (24) remote from the driven element (22) and bearing against the plug-on shaft (3).

21. The brush section according to claim 20, wherein the helical compression spring (27) is held by one of an enlargement (28) of the driving element (24) and a sleeve (33) press-fitted onto the driving element (24).

22. The brush section according to claim 15 wherein a helical compression spring (35) is arranged on the side of the driving element (24) close to the driven element (22) and bearing against the driven element (22) and the plug-on shaft (3).

23. The brush section according to claim 15, wherein a helical tension spring (37) is held on the side of the driving element (24) remote from the driven element (22) and on the plug-on shaft (3).

24. The brush section according to claim 15, wherein the driving element (24) and the driven element (22) are fixedly joined together.

25. The brush section according to claim 15 in combination with an electric toothbrush, the brush section adapted to be coupled therewith.

26. The brush section according to claim 15, wherein the transverse axis extends at an angle of about 90° to the longitudinal axis.

27. The brush section according to claim 15 wherein the driven element is arranged eccentrically to the transverse axis and the driving element is arranged eccentrically to the longitudinal axis.

* * * * *